(12) United States Patent
Isaka et al.

(10) Patent No.: US 8,149,410 B2
(45) Date of Patent: Apr. 3, 2012

(54) DETECTING DEVICE, DETECTING UNIT SUBSTRATE, DETECTING UNIT, DETECTING UNIT KIT AND DETECTING METHOD

(75) Inventors: Kazuo Isaka, Tokyo (JP); Satoru Nishiuma, Kawasaki (JP); Masaya Ogino, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 308 days.

(21) Appl. No.: 12/279,985

(22) PCT Filed: Mar. 20, 2007

(86) PCT No.: PCT/JP2007/056523
§ 371 (c)(1),
(2), (4) Date: Aug. 19, 2008

(87) PCT Pub. No.: WO2007/108556
PCT Pub. Date: Sep. 27, 2007

(65) Prior Publication Data
US 2010/0220328 A1    Sep. 2, 2010

(30) Foreign Application Priority Data

Mar. 20, 2006 (JP) ................................. 2006-077259
Mar. 12, 2007 (JP) ................................. 2007-062588

(51) Int. Cl.
*G01N 21/55* (2006.01)
*G01N 21/00* (2006.01)
(52) U.S. Cl. ............ 356/445; 422/61; 435/7.1; 435/7.2

(58) Field of Classification Search .......... 356/445–447, 356/72, 246, 317, 326; 250/573; 385/12–14, 385/147, 129, 141; 422/61, 68.1, 82.05; 257/433, 414; 435/88.7, 4, 6, 7.1, 7.2; 436/164, 436/172
See application file for complete search history.

(56) References Cited

U.S. PATENT DOCUMENTS

| 5,370,842 A | 12/1994 | Miyazaki et al. |
| 6,331,276 B1 * | 12/2001 | Takei et al. ................. 422/82.09 |
| 6,485,905 B2 * | 11/2002 | Hefti ................................. 435/6 |
| 6,539,156 B1 | 3/2003 | Dickson et al. |
| 7,079,250 B2 * | 7/2006 | Mukai ........................... 356/445 |

(Continued)

FOREIGN PATENT DOCUMENTS

JP    10-261244    9/1998
(Continued)

OTHER PUBLICATIONS

PCT International Search Report and Written Opinion of the International Searching Authority, mailing date Jun. 6, 2007 in PCT/JP2007/056523.

(Continued)

*Primary Examiner* — Sang Nguyen
(74) *Attorney, Agent, or Firm* — Fitzpatrick, Cella, Harper & Scinto (57) ABSTRACT

A necessary number of metal structures including a trapping body for trapping a target substance provided on a support are one-dimensionally placed to form a transmission path of plasmon, and a signal based on the plasmon transmitted on the transmission path is detected so as to detect whether or not there is trapping of the target substance from a sample to the trapping body. It is thereby possible to detect a reaction of the trapping body belonging to the detecting unit and the target substance with high sensitivity.

7 Claims, 8 Drawing Sheets

U.S. PATENT DOCUMENTS

| | | | |
|---|---|---|---|
| 7,271,914 B2 * | 9/2007 | Lin et al. | 356/445 |
| 7,387,901 B2 | 6/2008 | Nishiuma et al. | |
| 7,405,035 B2 | 7/2008 | Kawamura et al. | |
| 7,778,137 B2 * | 8/2010 | Hamada | 369/112.01 |
| 7,826,042 B2 * | 11/2010 | Yamamichi et al. | 356/72 |
| 7,839,508 B2 * | 11/2010 | Nishikawa et al. | 356/445 |
| 2004/0155309 A1 * | 8/2004 | Sorin et al. | 257/433 |
| 2004/0183176 A1 * | 9/2004 | Naya et al. | 257/680 |
| 2006/0011862 A1 | 1/2006 | Bernstein | |
| 2006/0170918 A1 | 8/2006 | Nishiuma | |
| 2007/0210268 A1 * | 9/2007 | Yamamichi et al. | 250/573 |
| 2007/0285666 A1 | 12/2007 | Utsunomiya et al. | |
| 2008/0225292 A1 | 9/2008 | Nishiuma et al. | |
| 2008/0316486 A1 | 12/2008 | Nishiuma et al. | |

FOREIGN PATENT DOCUMENTS

| | | |
|---|---|---|
| JP | 2000-356587 | 12/2000 |
| JP | 2004-191110 | 7/2004 |
| JP | 2004-285325 | 10/2004 |
| JP | 2005-283556 | 10/2005 |
| WO | 0113149 | 2/2001 |
| WO | 2005008222 | 1/2005 |
| WO | 2005085806 | 9/2005 |

OTHER PUBLICATIONS

PCT International Preliminary Report on Patentability, mailing date May 6, 2008 in PCT/JP2007/056523.

Nomura, et al., "Efficient optical near-field energy transfer along an Au nanodot coupler with size-dependent resonance", Appl. Phys. B, vol. 84, 2006, pp. 257-259.

Nomura, et al., "Nanodot coupler with a surface plasmon polariton condenser for optical far/near-field conversion", Applied Physics Letters, vol. 86, No. 18, 2005, pp. 181108-1-181108-3.

U.S. Appl. No. 12/088,023, International Filing Date Dec. 20, 2006, Yamamichi, et al.

U.S. Appl. No. 12/296,426, International Filing Date May 8, 2007, Handa, et al.

U.S. Appl. No. 12/159,391, International Filing Date Jan. 17, 2007, Nishiuma, et al.

Kajikawa, et al., "Biosensing by Localized Plasmon Resonance", Applied Physics, vol. 72, No. 12, 2003, pp. 1541-1544.

Kajikawa, et al., "Localized Plasmon Resonance Enhanced Optical Second-Harmonic Generation", Optics, vol. 33, No. 3, 2004, pp. 159-164.

* cited by examiner

DETECTING DEVICE, DETECTING UNIT SUBSTRATE, DETECTING UNIT, DETECTING UNIT KIT AND DETECTING METHOD

TECHNICAL FIELD

The present invention relates to a detecting device, a detecting unit, a detecting unit substrate and a detecting kit for detecting a target substance in a sample, and a target substance detecting method using the detecting unit.

BACKGROUND ART

Conventionally, a surface plasmon resonance sensor, for instance, has been used as an affinity sensor for detecting whether or not there is adsorption or coupling of substances, such as whether or not there is adsorption or coupling of an antigen in an antigen-antibody reaction.

In general, the surface plasmon resonance sensor comprises a detecting unit including a surface in contact with a test sample, means for light irradiation to the detecting unit and photo-detecting means for detecting reflected light from the detecting unit. The detecting unit comprises a prism and a metal film formed on a surface of the prism and contacting the sample. The light irradiation means includes a light source and an optical system which are placed to be able to acquire various angles of incidence of a light beam against an interface between the prism and the metal film. The photo-detecting means detects intensity of total reflected light reflected off the interface between the prism and the metal film as to each of the various angles of incidence by incidence of the light beam on the detecting unit.

However, the sensor has problems that its configuration becomes complicated because the detecting unit requires the prism as its component, and the detecting unit cannot be placed in a little place where the prism can hardly be placed.

The metal film formed on one surface of the prism in the detecting unit is generally formed by using a vacuum evaporation method. For that reason, a vacuum evaporator requires a special structure for vacuum-evaporating the metal film on a predetermined surface of the prism.

Development is underway as to various methods which utilize surface plasmon resonance using an attenuated total reflection method as above, and there are already commercialized products. As described above, however, it is difficult to miniaturize the sensor having the above configuration because the configuration of the optical system becomes complicated and restrictions on placement are strict.

As for these problems, there are proposals of various devices of simple configurations which are capable of detecting. The following are known for instance.

(a) Japanese Patent Application Laid-Open No. 2000-356587 discloses a sensor having a structure in which a metal structure is fixed like a film on the surface of a substrate. In this case, it detects adsorption or deposition of substances on the metal structure by emitting light to the substrate and measuring absorbance of a measuring beam transmitted through the metal structure on the backside of the substrate. This allowed the detecting by a simple device configuration with no need of the prism as a component. The publication also proposes a sensor utilizing an optical fiber as another example of the simple configuration.

(b) Applied Physics 72, 1541 (2003) reports a small sensor having practical-level sensitivity which has the metal structure deposited on an end face (effective diameter 50 μm) of the optical fiber.

(c) Japanese Patent Application Laid-Open No. 2004-191110 discloses a sensor which utilizes plasmon resonance having covered a fiber side face with a gold thin film.

The above (a) and (b) utilize localized plasmon resonance of the metal structure and (c) utilizes surface plasmon resonance of a metal thin film so as to allow highly sensitive detecting.

Here, in the configuration, the measuring beam is transmitted through one of particles placed with spacing just once and influenced by the plasmon resonance of only a single metal structure on the transmission thereof. The above (c) has the configuration in which the beam is reflected off the gold thin film on the fiber side face to be influenced by the plasmon resonance. In all the cases of the sensors of (a), (b) and (c), the light irradiation means is configured to have the measuring beam incident at an angle on a surface constituted by an arranged metal structure (thin film) or a metal thin film surface. According to this configuration, there is no concept that the beam transmits through the metal structure plural times or the beam effectively passes through only the metal structure so that interaction between the beam and the metal is reduced. For that reason, the ratio of a signal (change in light volume) light volume obtained by adhesion of substances to the metal structure obtained against the light volume of the beam incident on the substrate is small.

Japanese Patent Application Laid-Open No. 2005-283556 discloses an element for recognizing a target substance in a sample. The element has plural particles including metallic elements at least on the surface of a minute structure, and detects a change in properties of the particles based on the sum of the light outputted from the plural particles against irradiation of detecting beams. The detecting method disclosed by the publication is characterized in that high signal intensity can be obtained because signals from the plural particles are comprehensively detected. However, all the detecting beams entering all the sensors do not pass through the particles since a part of the detecting beams passes through a columnar portion of the minute structure or directly passes inside a flow path. Therefore, there remains a factor for lowering an S/N ratio.

In the above-mentioned detecting method using the sensor, it is required to improve detecting accuracy as to a phenomenon of which S/N ratio is small signal beam for detecting is small against background light). For that reason, it required a high-performance signal separation technique of a high dynamic range or a technique for separating the background light.

Under a condition that concentration of a target substance is lean, an area in which the target substance was coupled to a trapping body substance was narrow against a trapping body fixed on the element so that a signal was submerged and detecting of minute amounts became difficult.

DISCLOSURE OF THE INVENTION

An object of the present invention is to provide a detecting unit capable of detecting a reaction of a trapping body belonging to the detecting unit and a target substance with high sensitivity, a detecting device, a detecting method and a detecting kit using it and a substrate for obtaining the detecting unit.

The present invention has been made in view of various problems of the conventional techniques described above, and provides a highly-sensitive detecting method of a higher S/N ratio than these detecting methods and capable of detecting minute amounts. The present invention also provides a localized plasmon sensor which allows placement in a little place by miniaturization and simple signal processing.

The present invention is directed to a detecting device for detecting a target substance or measuring an amount of the target substance in a sample by localized surface plasmon resonance, comprising:

a detecting unit including a support, plural metal structures placed on the support and a trapping body for trapping the target substance in the sample;

a light irradiation means for emitting light to the detecting unit; and a plasmon detecting means for detecting a signal based on plasmon generated by light irradiation to the detecting unit, characterized in that:

the plural metal structures are adapted for a transmission path on which the plasmon is one-dimensionally transmitted; and the plasmon detecting means is provided at a position capable of detecting a signal based on the plasmon transmitted on the transmission path.

The light irradiation means can be placed to have the light incident on the transmission path comprised of the plural metal structures from a direction nonparallel therewith.

The plasmon detecting means can include a means of detecting light for detecting the light based on the plasmon, and the light based on the plasmon transmitted on the transmission path is received by the means of detecting light.

The light irradiation means and the means of detecting light can be placed so as not to have the same optical axis.

The means of detecting light can have a part for converting the light based on the plasmon transmitted on the transmission path to far-field light and photoelectrically converts the converted far-field light.

The means of detecting light can photoelectrically convert the light based on the plasmon transmitted on the transmission path in a state of a near-field light in proximity to the transmission path.

The plural metal structures can be arranged on a surface of the support at a pitch of array of 1 to 10 times the size of the metal structures.

The arrangement of the metal structures can be comprised of a spectrum shaping function part and a detecting function part.

In the detecting device, an output of the transmission path having a different number of arrangements comprised of the metal structures can be detected on an equivalent condition.

In the detecting device an electromagnetic field response of the metal structures can have a directivity in a transmission direction.

The present invention is directed to a substrate of a detecting unit for detecting a target substance in a sample by localized surface plasmon resonance, comprising:

a support;

plural metal structures placed on the support; and a conversion means for converting intensity of plasmon generated by light irradiation to the metal structures to a detectable physical quantity, characterized in that:

the plural metal structures are adapted for a transmission path on which the plasmon is one-dimensionally transmitted; and the conversion means is provided at a position capable of converting the intensity of the plasmon transmitted on the transmission path to a detectable physical quantity.

The detectable physical quantity can be an intensity of far-field light.

The detectable physical quantity can be an intensity of near-field light.

The plural metal structures can be arranged on a surface of the support at a pitch of array of 1 to 10 times the size of the metal structures.

In the detecting unit substrate, an electromagnetic field response of the metal structures can have directivity in a transmission direction.

The present invention is directed to a detecting unit for detecting a target substance in a sample by utilizing localized surface plasmon resonance, characterized in that a trapping body for trapping the target substance is fixed on the detecting unit substrate.

The present invention is directed to a target substance detecting kit for detecting a target substance or measuring an amount of the target substance in a sample, characterized by comprising:

the detecting unit substrate;

a trapping body of the target substance; and a reagent for trapping the target substance with the trapping body.

The present invention is directed to a target substance detecting kit for detecting a target substance or measuring an amount of the target substance in a sample, characterized by comprising:

the detecting unit; and a reagent for trapping the target substance with the trapping body.

The present invention is directed to a method for detecting a target substance or measuring an amount of the target substance in a sample by localized surface plasmon resonance, characterized by comprising the steps of:

bringing the sample into contact with the detecting unit; and detecting the trapping of a target substance to a trapping body belonging to the detecting unit via plasmon generated by light irradiation to the detecting unit and one-dimensionally transmitted to a transmission path belonging to the detecting unit.

Further features of the present invention will become apparent from the following description of exemplary embodiments with reference to the attached drawings.

BEST MODES FOR CARRYING OUT THE INVENTION

A target substance detecting device according to the present invention comprises at least a detecting unit including a trapping body of a target substance and plural metal structures, light irradiation means and plasmon detecting means. The target substance detecting device detects whether or not there is a target substance or an amount of the target substance in a sample by utilizing localized surface plasmon resonance. The plural metal structures placed in the detecting unit constitute a transmission path for one-dimensionally transmitting localized surface plasmon (hereinafter merely referred to as the plasmon) generated by light irradiation. The transmission path is formed by one-dimensionally (linearly for instance) arranging the plural metal structures on a support via predetermined spacing. On the transmission path, one-dimensional transmission of the plasmon is attained by transmitting the plasmon excited by light irradiation to a certain metal structure to a metal structure placed adjacently to the metal structure. The plasmon having been thus one-dimensionally transmitted on the transmission path is detected by the plasmon detecting means. Thus, it is detected by the detecting means separately from background light by utilizing the transmission path and based on a detecting signal so as to allow highly sensitive detecting even in a measurement system of a small S/N ratio.

For instance, in the case where the one-dimensionally transmitted plasmon is converted to light, which is received by means of detecting light and detected, the means of detecting light is placed in the device so as to mainly measure the light transmitted over the transmission path composed of the plural metal structures. Furthermore, the light irradiation means is placed to be incident on the transmission path composed of the plural metal structures from a direction nonparallel with the transmission path. It is preferable to place the means for emitting light to the metal structures and the means of detecting light so that they will not have the same optical axis. It is possible, by such placement of the light irradiation means and the means of detecting light, to more effectively separate the detecting signal based on the plasmon from the background light.

There are also the cases where the light irradiation means emits broadband white light other than the case of letting in single-wavelength light suited to excitation of the plasmon transmitted over the transmission path. The transmission path composed of the metal structures shows transmission characteristics which are decided by a form and a pitch of array of the metal structures. To be more specific, even in the case where the plasmon is excited by irradiating a white light source, the plasmon propagates being filtered due to the characteristics of the transmission path. It is possible, by utilizing this quality, to form a spectrum of the light accompanying the plasmon. To be more precise, as a structure, the range having the metal structure on a light incidence side of the transmission path is used as a filter (spectrum forming part), and the light is transmitted to the transmission path (detecting function part), adjacent to the range, where a plasmon resonance condition changes due to adsorption of the target substance so as to measure whether or not there is the adsorption of the target substance as a change in transmission intensity. It is possible, by forming the spectrum, to have a characteristic wherein the change in the plasmon resonance condition greatly influences the transmission intensity so as to contribute to higher sensitivity.

In the above case, a trapping body substance may be fixed only on the detecting function part. In the case of using the transmission path composed of a uniform metal structure, however, propagation efficiency is reduced on a border between the spectrum forming part and the detecting function part because the plasmon resonance condition is different depending on whether or not there is the trapping body substance. As a setup, the propagation efficiency should be maximum at a certain wavelength on the transmission path prior to adsorption of a detected substance. Thus, as for the spectrum forming part which needs no trapping body substance, adjustments should be made as to the size and the pitch of array of the metal structures constituting the transmission path so that the resonance condition will be similar to the metal structures having the trapping body substance fixed thereon. Consequently, it becomes no longer necessary to fix the trapping body substance on the metal structures unrelated to detecting sensitivity, which can save the trapping body substance.

Hereunder, preferred embodiments of the configurations of the present invention will be further described.

Device Configuration (1) Configuration for Efficiently Coupling the Light by Using an Optical Waveguide The light irradiation means includes an optical system for emitting the light from the light source to an area where the metal structures of the detecting unit are placed. It may have either a configuration composed only of the optical system and used by connecting to a separately provided light source when used or a configuration having the light source integrated with the optical system.

There are various methods of having the light efficiently enter the metal structures of a substrate. It is possible to introduce the light to the metal structures by sharpening an end of an optical fiber and taking consistency of phases via a metal thin film on the support or by directly contacting or very closely approaching to the metal structures. There are various other methods of conversion, and plural methods are introduced in Optics Vol. 33, No. 3 (2004).

Figure 1:
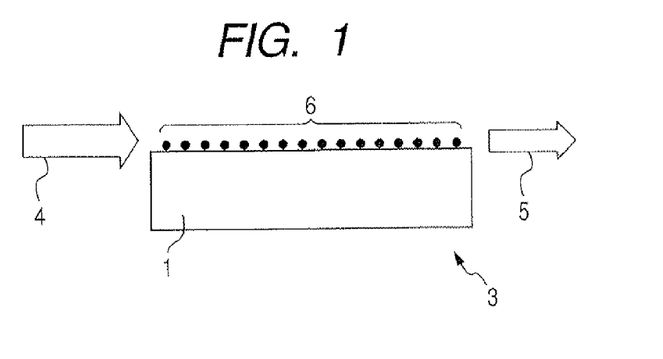
FIG. 1 is a diagram for describing a first overview related to the present invention.
Figure 2:
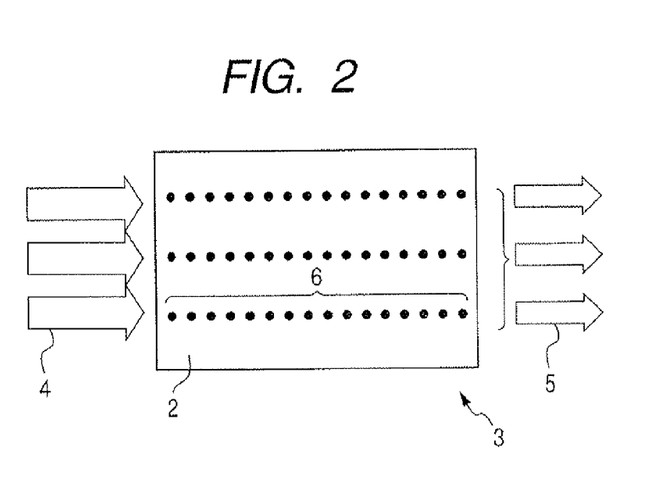
FIG. 2 is a diagram for describing a second overview related to the present invention.

A transmission path capable of one-dimensional transmission of the plasmon is formed by plural metal structures in an area where the metal structures of the detecting unit to which light from the light irradiation means is emitted are placed. FIG. 2 shows an example designed to configure plural transmission paths 6 with metal structures 2. FIG. 1 shows a sectional view in a thickness direction of a support along one transmission path. It is thereby possible to increase an outgoing light volume and improve sensitivity. In this case, it is also possible to cover the metal structure of each transmission path with a different dielectric material corresponding to a detected substance so as to simultaneously detect plural kinds of substances. An interval between the transmission paths (interval between neighboring metal structures in a non-transmission direction) in the case of thus juxtaposing the plural transmission paths 6 is also influenced by the form of the metal structures and the like. In general, the metal structures form near fields of approximately their own size in their vicinity. However, integration is possible while alleviating influence of interaction between the neighboring transmission paths by designing the metal structures in a structure where an electromagnetic field response of the metal structures has directivity and arranging them in consideration of a direction of the directivity.

The transmission path can be configured by plural metal structures or preferably three or more metal structures, where the number thereof is selectable according to performance and size of the device. In the case of a system of which transmission characteristics of the transmission paths are strongly influenced by a change in refractive index, signals become equivalent when a target substance of a certain degree or over is trapped. To discriminate them, it is possible to expand a dynamic range of detecting by bringing the target substance into contact with the transmission path having a different number of arrangements of the metal structures on an equivalent condition.

In the case where an incidence area of the light is smaller than that of the element disclosed in the aforementioned Japanese Patent Application Laid-Open No. 2000-356587 in the present invention, the light volume can be effectively exploited by converging the light from the light source and having it enter the detecting unit.

Figure 7A:
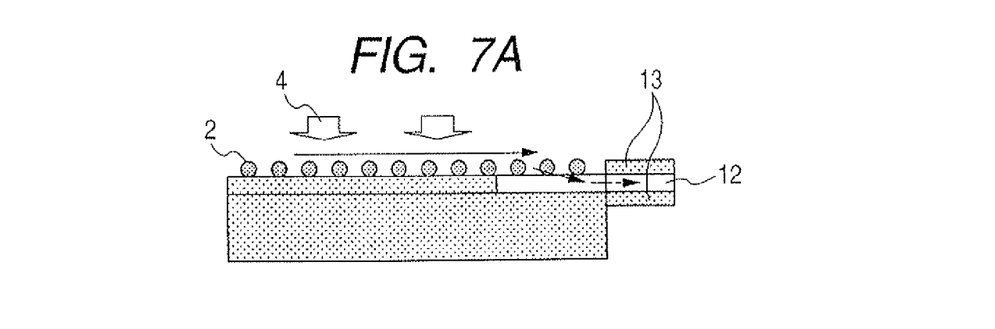
FIGS. 7A, 7B and 7C are diagrams for describing an embodiment related to the present invention.
Figure 7B:
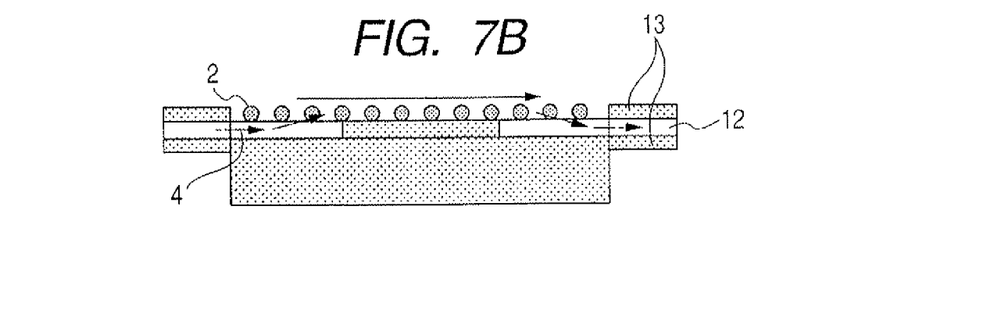
Figure 7C:
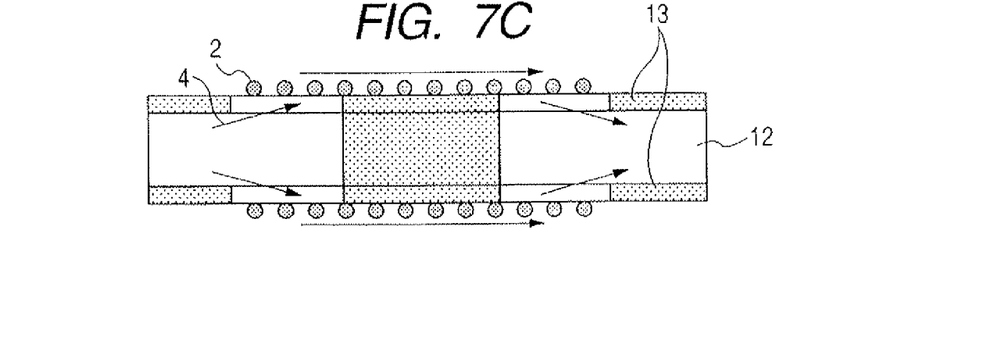

There is no problem if the configuration for having the light from the light irradiation means enter the metal structures is the configuration for coupling the light to the metal structures by using an optical waveguide. FIGS. 7A, 7B and 7C describe a technique thereof. FIG. 7A is a sectional view in the thickness direction of the support along the transmission path, which shows a state where light irradiation is performed by specifying a position in the transmission path. In comparison, FIG. 7B shows an appearance wherein the light transmitted through a core layer 4 of the optical fiber is coupled to a metal structure 2 installed in a clad layer and generates the plasmon. The plasmon excited in the metal structure is transmitted to a neighboring metal structure by dipolar interaction and the like so as to eventually guide the light to a core layer 12 of the optical fiber.

In FIG. 7C, the clad layer around the metal structures is a material of a low refractive index to couple the light transmitted through a core layer 4 to the metal structure 2. The plasmon which has been transmitted among the metal structures through the dipolar interaction and the like is converted to the light again at an extreme end and led to the core layer 12 of the optical fiber.

FIGS. 7A and 7B show the structure of a detecting unit provided with an area where the metal structures are provided on a predetermined surface of a tabular support and an optical waveguide for taking out the plasmon as the light. FIG. 7C shows an example of the detecting unit configured like an optical fiber. FIGS. 7A and 7B may also have the configuration like an optical fiber of which cross-section is round while FIG. 7C may have a tabular configuration where the cross-section is rectangular.

(2) Configuration for Having the Light Vertically Enter the Sensor

Figure 8A:
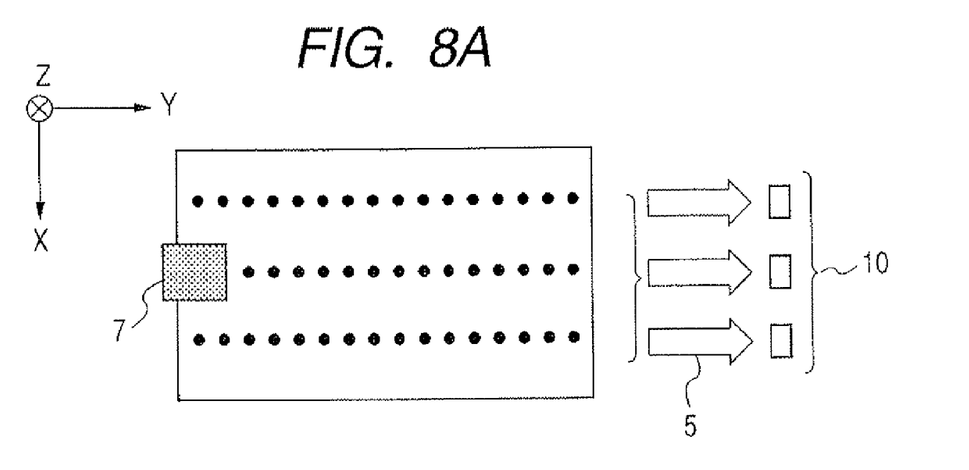
FIGS. 8A and 8B are diagrams for describing an embodiment related to the present invention.
Figure 8B:
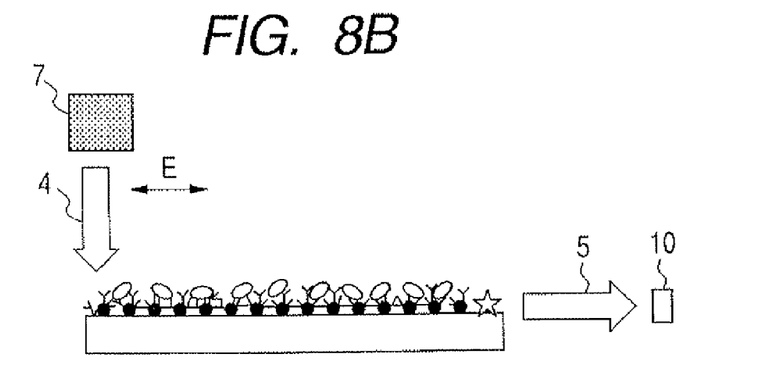
Figure 9A:
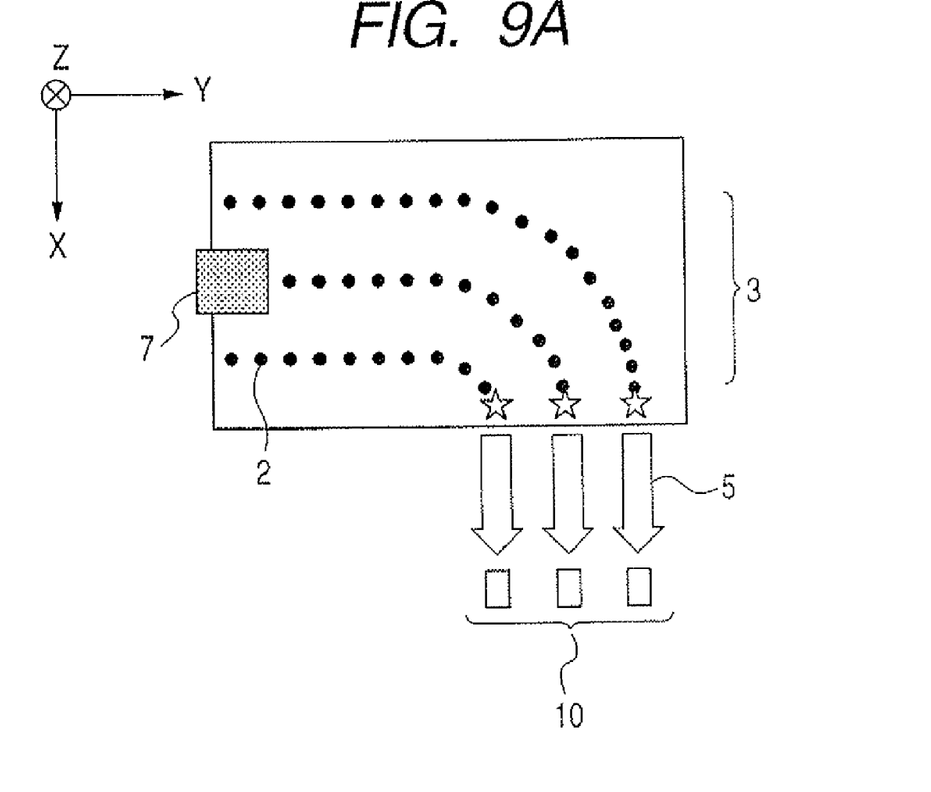
FIGS. 9A and 9B are diagrams for describing an embodiment related to the present invention.
Figure 9B:
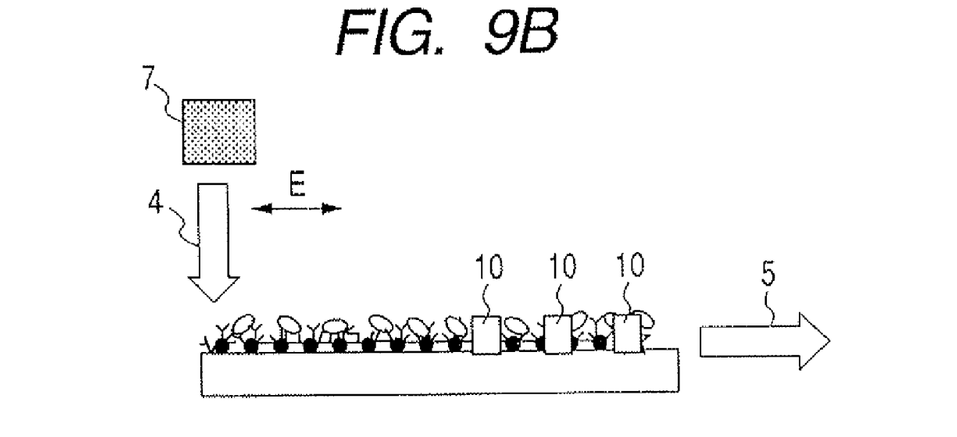

A configuration for having incident light enter the sensor from a vertical direction is also possible (FIG. 8A and its side view 8B, FIG. 9A and its side view 9B). As shown in the drawings, the light deviated in approximately the same direction as the direction in which the metal structures are arranged is introduced so that only the light having interacted with the metal structures can be transmitted as the plasmon to a neighboring metal structure.

As for the transmitted plasmon, there is a method of converting it to far-field light (photoelectric conversion) at the end of the transmission path and detecting its intensity. In this case, a structure for disordering the near field accompanying the plasmon should be placed at the end of the transmission path. It is also possible to directly detect near-field light accompanying the plasmon by forming a photodiode area such as a PN junction in proximity to the structures. There is also no problem in fixating illuminants such as fluorescent molecules on the metal structures and converting it to the light via the fluorescent molecules. Furthermore, there is no problem in detecting energy transmitted as the plasmon as a current pulse. Here, it is desirable to adopt a technique of fixating the fluorescent molecules and converting it to the light.

A plasmon detecting means has the configuration capable of detecting a signal based on the plasmon described above, which can have a configuration according to various conversion formats. In the case of converting the plasmon to the light and detecting it, the detecting means (such as a photosensor) can be configured to form the means of detecting light, an output device for outputting a signal from the means of detecting light as a detecting signal, and the like.

It is possible, by taking the configuration for performing optical detecting, to mainly guide the light via the metal structures to the sensor and reduce the background light. Here, it is desirable to set the light from the metal structures at the intensity (20% or more of received light signals is the light from the metal structures) capable of acquiring the SN ratio to the light from a background component such as stray light.

(3) Configuration Provided with Apertures for Light Interception

Figure 13A:
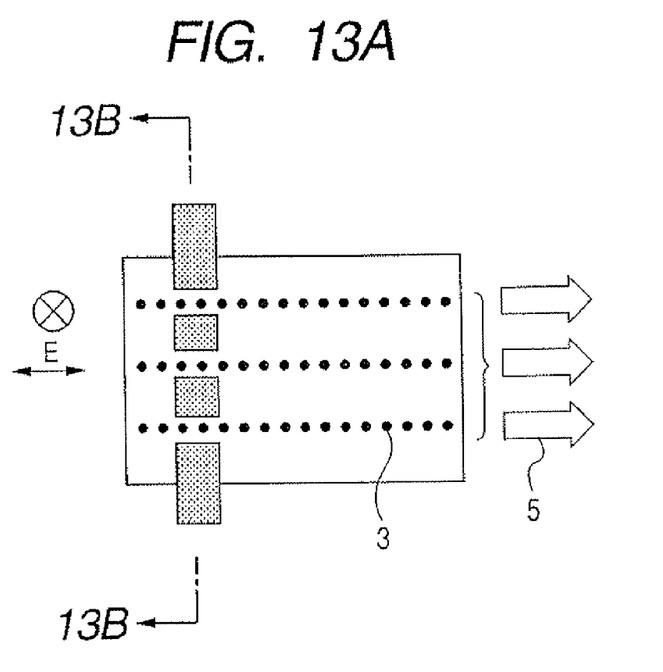
FIGS. 13A and 13B are diagrams for describing an embodiment related to the present invention.
Figure 13B:
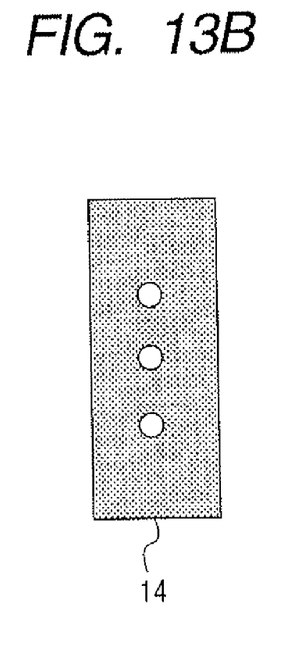

It is also possible to have a configuration which intercepts the incident light not used for plasmon excitation with apertures and reduces the background light. FIGS. 13A and 13B show the configuration which limits the incident light with apertures 14, intercepts the light not coupling to the metal structures and eventually converts the plasmon transmitted via metal structures 2 to the light to guide it to the photosensor. It is possible, by taking this configuration, to almost completely intercept the light which does not interact with the metal structures. Here, it is possible to have a configuration in which the light from the metal structures has stronger intensity (50% or more of the entire light signals is the light from the metal structures) than the light from the background component such as stray light.

Method of Creating the Sensor

There is no problem whatever technique is used as to an arrangement method of the metal structures. Some examples will be described here.

(1) Method of Forming Metal Particles on the Support by Evaporation

It is possible to arrange and fix small gold particles as the metal structures by depositing carbon projections with a focused ion beam system at predetermined intervals in a predetermined area of a support such as a silicon substrate and then evaporating gold by sputtering.

(2) Method of Using a Pattern for Arrangement of the Metal Structures

It is also an effective method to directly arrange and fix the metal structures by heretofore known methods such as those disclosed in Japanese Patent Application Laid-Open No. H10-261244 and Japanese Patent Application Laid-Open No. 2004-285325. To be more precise, it is possible to form a minute pattern of concavities and convexities of predetermined intervals, width and thickness on the support and form the metal structures on the minute pattern so as to arrange and fix the metal structures. It is also possible to form a minute pattern of hydrophilic areas and hydrophobic areas of predetermined intervals and width on the support so as to arrange and fix the metal structures correspondingly to the minute pattern.

(3) Method by Electron-Beam (EB) Printing

Patterning is also possible by electron-beam (EB) printing. A Ti layer (not shown) is film-formed as a binder layer on a quartz substrate as the support, and then an Au layer is continuously film-formed. Next, a negative type resist is spin-coated to provide a resist layer. After performing a prebake, it is introduced to a chamber of an electron-beam printing device so as to draw a desired pattern on the resist layer. After finishing the drawing, a post-exposure bake is performed and it is quenched. Thereafter, it is developed with a developer, and the resist layer is patterned. Dry etching is performed with the patterned resist layer as a mask, and the pattern is transferred on a gold layer to obtain nanodots. After patterning gold, a process such as a remover is lastly performed to eliminate the resist layer on the nanodots. It is possible, by undergoing the above process, to form a gold pattern characterized by being arranged and fixed at predetermined intervals on the surface of the substrate as shown in FIGS. 8A and 8B.

The support may be any support which can place the metal structures in a predetermined arrangement without causing a difficulty to the measurement intended by the present invention. Furthermore, it is possible, as described in FIGS. 7A, 7B and 7C earlier, to use the support having the optical waveguide built on a base. As for the support or the base, it is possible to use one composed of a resin such as silicon, quartz, glass or polycarbonate or a complex thereof.

Here, the metal structures may be in various forms. For instance, they may be formed in the forms such as spherical particles and rod-like particles. Length of the plasmon of the metal structures in one-dimensional transmission direction (a diameter D in the case of a spherical form; length of a long axis in the case where it is rod-like and its long-axis direction is in the transmission direction) should desirably be in the range of 5 nm to 1 µm or so. The length of the metal structures in a non-transmission direction is selected as appropriate according to the characteristics of the device and a formation method of the metal structures.

It is also desirable that the transmission path be formed by arranging plural metal structures in the same form and size.

Furthermore, it is possible to eliminate influence of disturbance noise such as intensity fluctuation of the light source by implementing an arrangement which can simultaneously detect a signal transmitted over the transmission path composed of the metal structures in contact with the target substance and a signal not in contact therewith.

As described above, the spherical form can be named as a three-dimensional form of the metal structures. However, it may also be irregular-shaped particles such as a triangle and a square or a nanorod of which horizontal and vertical aspect ratio is 1 or more. Furthermore, it may be in layers of which cross-section is rectangular. The present invention also includes as its concept the case where substantial particles are formed on the substrate by etching or deposition on the surface of the support as long as it does not depart from the scope thereof.

Here, it is necessary to one-dimensionally place the number of the metal structures necessary to secure the length of the transmission path at the intervals at which localized plasmon exists. The intervals should desirably be within similar order to the length of the metal structures in the transmission direction (a diameter D in the case of a spherical form; length of a long axis in the case where it is rod-like and its long-axis direction is in the transmission direction). To be more precise, the metal structures are arranged at the pitch of array of 1 to 10 times the size of the metal structures. The transmission path composed of the metal structures efficiently transmits only a specific wavelength decided by the size and pitch of array of the metal structures. Because of this characteristic, the form and pitch of array of the metal structures are decided according to the required wavelength (here, one-dimensionally means the configuration having the metal structures one-dimensionally (linearly) arranged against the transmission direction of the plasmon, and so it does not have to be a straight line but may also be an arrangement which is bending in the middle).

The metal structures can be adopted without limitation as long as they are the structures composed of gold, silver, copper or other metals capable of exciting the plasmon. In view of manufacturability, durability against a sample solution for detecting and the like, it is desirable to use small gold particles as the metal structures. Small silver particles have an advantage of allowing a sensitive measurement.

Principle of Detecting

1. Mechanism for Detecting the Target Substance with Good S/N

It is possible to configure a localized surface plasmon (LSPR) sensor by fixating a trapping body on an array of the metal structures (such as gold nanodot array) on the substrate made in the above process. To be more specific, the trapping body which uniquely reacts to an antigen as a detecting subject is fixated on the gold nanodots so that an antibody thereof traps the antigen as a target substance. After the reaction, permittivity of a medium among the gold nanodots changes so that a transmission condition of the plasmon changes and the transmission intensity changes. To be more specific, it is possible, by monitoring the intensity of the transmitted plasmon, to detect concentration of the target substance. The trapping body can be coupled to the metal structures by using a heretofore known method according to the types of the trapping body and the metal structures.

2. Mechanism for Transmitting the Plasmon Among the Metal Structures

As a measuring beam is transmitted with the portion composed of the plural metal structures arranged here as the transmission path, plasmon resonance among the metal structures can be effectively utilized. Consequently, it is possible to detect with high accuracy a change in absorbance due to adsorption and deposition of the substances by the metal structures of the detecting unit.

The transmission path refers to a path on which the light is transmitted among the metal structures due to the interaction of the localized plasmon. Transmission efficiency of the plasmon transmitted over the transmission path depends on at what intervals and how the metal structures are placed. According to Appl. Phys. B84 257-259 Nomura et. al for instance, gold dot transmission paths of various diameters and pitches of array were made based on diameters 2 a and pitch of array 2.4 a. It is reported that, as a result of measuring near-field light intensity at the end of the transmission path by emitting the light of 785 nm wavelength, the plasmon (near-field light accompanying it) is most efficiently transmitted by the gold dot transmission path of which diameter is 200 nm and pitch of array is 240 nm.

The detecting unit of the present invention is characterized by positively exploiting the plasmon transmitted among the plural metal structures. The present invention detects the refractive index of the medium existing in proximity to the surface of the metal structure fixed on the support, i.e. up to the distance of the diameter of the metal structure fixed on the substrate for instance. Therefore, it is possible, in the case where the detecting unit is placed in a liquid, to measure the refractive index of the liquid in proximity to the detecting unit.

Figure 3:
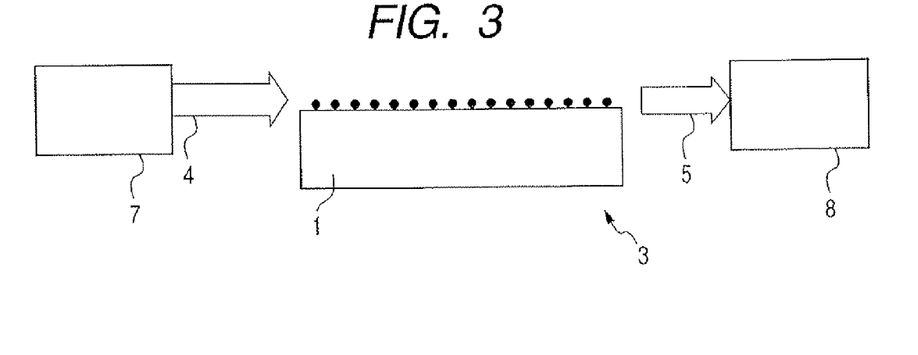
FIG. 3 is a diagram for describing an embodiment related to the present invention.

FIG. 1 shows a conceptual explanatory diagram of a localized plasmon resonance sensor according to the above-mentioned present invention. A detecting unit 3 is configured by arranging and fixing the necessary number of plural metal structures 2 such as gold and silver as a transmission path 6 on a support 1. FIG. 3 shows an overview of the measurement by the detecting unit 3 of the configuration in FIG. 1. As shown in FIG. 3, an incident light 4 emitted from a light source 7 enters the metal structures 2 on the surface of the support 1 of the detecting unit 3, transmits through the transmission path 6 and is then emitted outside as an outgoing light 5. Here, if the absorbance for each wavelength is acquired by measuring an absorption spectrum of the outgoing light 5 having transmitted through the metal structures 2 through use of a spectrophotometer, a resonant peak appears at a predetermined wavelength due to a relation between the permittivity of the metal structures 2 and the permittivity of a neighboring medium because of a localized plasmon phenomenon. As the refractive index of the medium existing in proximity to the metal structures 2 becomes higher, the absorbance of the resonant peak becomes higher and shifts to a long-wavelength side. This can be detected as a change in a transmitted light volume by measuring the change in the absorbance with an actinometer 8 as to the light of only a specific wavelength by means of a band pass filter or the like. The band pass filter is not necessary in the case of using a laser as the incident light.

The condition of localized plasmon resonance is complicated in the case where the metal structures are arranged. The condition of the localized plasmon resonance is as follows if it is shown based on the metal structure which is isolated and sufficiently smaller than the wavelength of the light.

Here, it is assumed that the metal structure is spherical. A minute spherical metal structure of a radius a having a complex permittivity $\in m (\lambda)$ is put in the medium of a complex permittivity $\in 0 (\lambda)$. Polarizability $\alpha (\lambda)$ of the metal structure is given by a formula (1).

$$\alpha(\lambda)=4\pi a^3(\in m(\lambda)-\in 0(\lambda))/(\in m(\lambda)+2\in 0(\lambda)) \quad (1)$$

The localized plasmon gets in a resonance state at the wavelength $\lambda$ at which an absolute value of a denominator of the formula (1) becomes minimum so that the size of the polarizability becomes maximum.

Consideration is given to a structure of a biosensor in which ligand molecules as a dielectric layer cover the metal structures. Adsorption of an analyzer in the liquid onto the ligand due to an interaction corresponds to equivalent increase in film thickness of the dielectric material. Thus, it is possible to analytically acquire the polarizability a ($\lambda$) as a whole even in the case of the structure in which the dielectric layer covers the metal structures.

Therefore, according to the present invention, it is possible, by measuring the absorbance of the outgoing light 5 emitted from the detecting unit 3, to detect the refractive index of the metal structures including the medium in proximity to the surface of the metal structures 2. Consequently, it becomes possible to detect the state of adsorption and deposition of the substances to the plural metal structures 2 fixed on a substrate 1 of the detecting unit 3.

The detecting unit according to the present invention can be made by fixing the trapping body for trapping a target substance on the substrate which has the transmission path formed by placing the necessary number of the metal structures on the support. The trapping body is selectable according to the kind of target substance. For instance, in the case where one of a unique coupled pair is the target substance, one of them can be utilized as the trapping body. As for such combinations, antigen/antibody, complementary DNA pair, receptor/ligand and enzyme/substrate can be named. As for the target substances, there are biologic materials (protein, nucleic acid, sugars, fat and the like), allergen, bacteria, viruses and the like.

It is possible to configure a target substance detecting kit by using the above detecting unit substrate, trapping body and a reagent (a buffer solution, a reagent for sample preparation or the like) for trapping the target substance for the trapping body. It is also possible to configure a detecting kit by using the detecting unit and the reagent (a buffer solution, a reagent for sample preparation or the like) for trapping the target substance for the trapping body.

EXAMPLES

Hereunder, a detailed description will be given with reference to the attached drawings as to examples of embodiments of the localized plasmon resonance sensor according to the present invention. However, they show illustrative embodiments, and the present invention is not limited thereto.

Example 1

An example related to the present invention will be described below. As shown in FIG. 3, the localized plasmon resonance sensor comprises a detecting unit 3, a light source 7 for letting the light into the detecting unit 3, and an actinometer 8 for acquiring absorbance by measuring an absorption spectrum of the light having transmitted through the detecting unit 3.

Here, the detecting unit 3 was made by using a detecting unit substrate having a large number of small gold particles (spherical) of 120 nm diameter arranged and fixed on a silicon substrate 1.

To be more precise, the small gold particles were arranged as follows.

Multiple carbon projections of which projection diameter is 120 nm were deposited at intervals of 70 nm with a focused ion beam system on the silicon substrate as the support, and then gold was evaporated to film thickness of 120 nm by sputtering so as to substantially arrange and fix the small gold particles at regular intervals.

In the above configuration, if the substances are adsorbed or deposited on the small gold particles after arranging the small gold particles, the absorbance of transmitted light changes. Only specific wavelengths centering on 550 nm were transmitted by the band pass filter so as to detect the change in the absorbance as the change in a transmitted light volume with the actinometer 8.

Figure 5A:
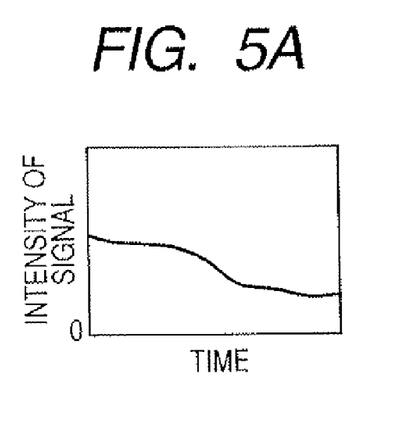
FIGS. 5A and 5B are diagrams about measurement results for describing the embodiment and the comparative example related to the present invention.

FIG. 5A shows this. As an acrylic resin is deposited on the substrate, the absorbance of the resonant peak becomes higher so that a deposited amount of the acrylic resin can be effectively detected due to reduction in the amount of light received.

In this example, the incident light transmits through plural metal structures before passing through the detecting unit. Therefore, it is significantly undergoes changes in optical characteristics around the metal structures so that high sensitivity can be obtained even if an incident light volume to the detecting unit is small.

It is considered that improvement in sensitivity in this configuration is schematically based on the following theory when taking as an example the case of taking out the light based on the plasmon as a signal.

The transmission efficiency of the plasmon transmitted from one metal structure constituting the transmission path to an adjacent metal structure is influenced by the plasmon resonance conditions of the metal structures, i.e. the permittivity of the metal, the structure, the pitch of array, surrounding permittivity and the like. In the case where a concrete structure is made, the permittivity of the metal, the structure and the pitch of array are fixed so that they are not the cause of a fluctuation of the plasmon transmission efficiency. For that reason, it is possible to measure the permittivity of the surrounding of the metal structures by measuring the fluctuation of the plasmon transmission efficiency, i.e. the near-field light intensity accompanying the plasmon. According to the structure of the plasmon transmission path of the present invention, an intensity change due to the fluctuation of the transmission efficiency in the case where the plasmon transmits over plural metal structures is a total of the fluctuations of the following three efficiencies. 1) Conversion efficiency to the plasmon on the metal structure surface on which irradiating light constitutes the transmission path, 2) transmission efficiency of the plasmon between adjacent metal structures, and 3) conversion efficiency to a physical quantity detectable from the plasmon at the end of the transmission path. There are as many parts related to the conversion of 2) as the intervals in the arrangement of the metal structures. It can be considered that, in the case where the transmission path is formed by N pieces of structure, the intensity change becomes n−1 th power compared to the case of one interval (between two structures). It is possible, due to this integrating effect, to amplify and detect the change in the plasmon transmission efficiency due to the change in the permittivity owing to the coupling of the target substance occurring around each individual structure so as to realize highly sensitive detecting.

Figure 6:
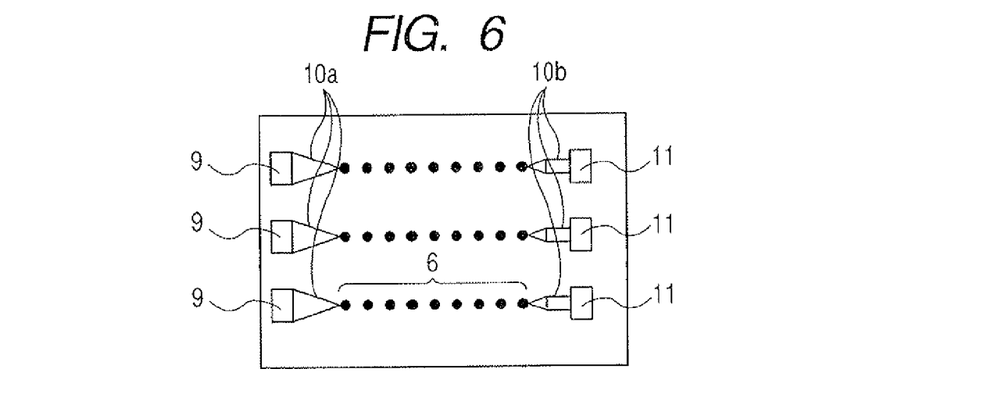
FIG. 6 is a diagram for describing an embodiment related to the present invention.

Next, a description will be given based on FIG. 6 as to an application to a sensor to which the present invention is applied. The sensor related to this application is composed of a detecting unit composed of a support 1 and a transmission paths 6, semiconductor laser light sources 9 placed on a substrate 1, collecting members 10 and photosensors 11. On the support 1, the light emitted from the semiconductor laser light sources 9 is collected by the collecting members 10 composed of a metal thin film or the like so as to enter and transmit over the transmission paths 6 composed of the metal structures. After transmitting over each of the transmission paths, the light is collected on each of the photosensors 11 by the collecting members 10, where a change in the absorbance due to attachment of the substances on the metal structures is detected.

It is possible, by having the above configuration, to detect a change in chemical properties as to a different substance on each of the transmission paths. In addition, it is possible to provide a convenient sensor of which light sources to photometer are integrated with no need to collect the light of each individual sensor with an optical system such as a prism.

Comparative Example

Figure 4:
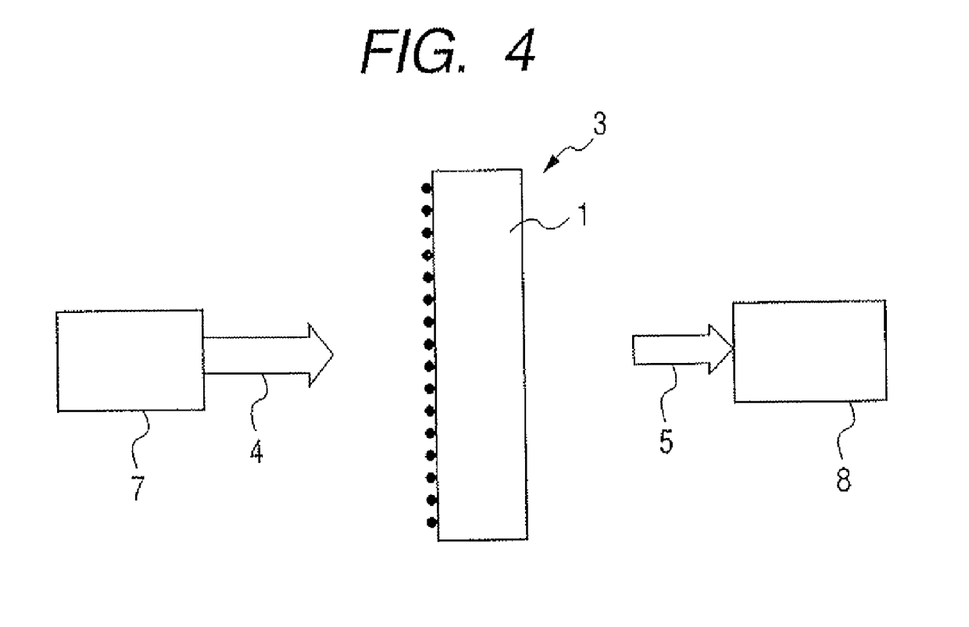
FIG. 4 is a diagram for describing a comparative example related to the present invention.

Hereunder, a comparative example to the example 1 related to the present invention will be described with reference to FIG. 4.

The localized plasmon resonance sensor of this comparative example comprises a detecting unit 3, a light source 7 such as a laser for letting the light into the detecting unit 3, and an actinometer 8 for measuring the absorption spectrum of the light transmitted through the detecting unit 3 and acquiring the absorbance. Here, the detecting unit 3 was made by arranging and fixing a large number of small gold particles of 30 nm diameter on the support 1 made of glass. As for application of the small gold particles, it was performed by immersing them in a 3-aminopropyltrimethoxysilane 10% methanol solution for several minutes and then washing and further immersing them in a colloidal gold solution of 30 nm diameter for several hours.

As described above, if the substances are adsorbed or deposited on small gold particles after two-dimensionally arranging (i.e. planately arranging) the colloidal small gold particles on the support 1, the absorbance of the transmitted light changes. Only the specific wavelengths centering on 550 nm were transmitted from the transmitted light by the band pass filter so as to detect the change in the absorbance as the change in a transmitted light volume with the actinometer 8.

Figure 5B:
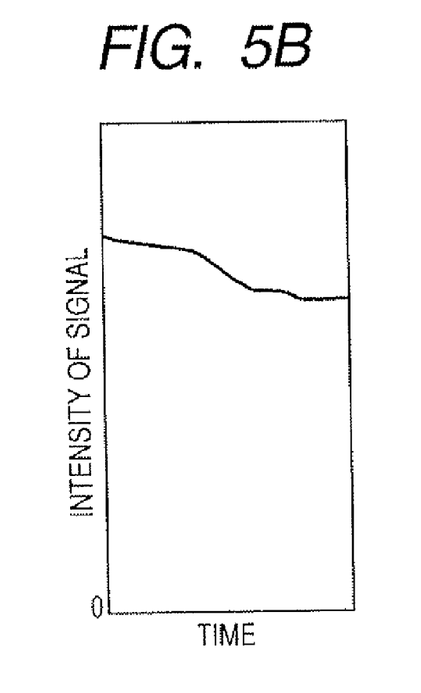

FIG. 5B shows this. As PMMA (polymethyl methacrylate) is deposited on the substrate, the absorbance of the resonant peak becomes higher so that the amount of received light of the actinometer 8 gradually decreases. In this comparative example, an initial light volume before deposition of the acrylic resin is large whereas the change in the light volume due to the deposition is small and so the S/N ratio is also small.

Example 2

An example related to the present invention will be described below.
Device Configuration As shown in FIGS. 8A and 8B, the localized plasmon resonance sensor comprises a detecting unit 3, a light source 7 for letting the light into the detecting unit 3, and an actinometer 8 for measuring the absorption spectrum of the light transmitted through the detecting unit 3 and acquiring the absorbance. Here, as for the detecting unit 3, a large number of small gold particles of 120 nm diameter are arranged and fixed on a quartz substrate 11. The light source 7 is installed in a direction vertical to the detecting unit so that the placement allows polarized light to be emitted in a direction parallel with a row direction of the gold nanodot array. The sensor is installed around an illuminant placed at the end of an opposite direction to irradiated dots of the gold nanodot array.
LSPR Sensor To be more precise, the small gold particles were arranged as follows. A Ti layer is film-formed by 5 nm as a binder layer on a quartz substrate as the support, and then an Au layer is continuously film-formed by 50 nm. Next, a negative type resist (SAL 601, Shipley Far East) is spin-coated to provide a resist layer. After performing a prebake, it is introduced to a chamber of an electron-beam printing device so as to draw a desired pattern on the resist layer. After finishing the drawing, a post-exposure bake is performed and it is quenched. Thereafter, it is developed with a developer, and the resist layer is patterned. Dry etching is performed with the patterned resist layer as a mask, and the pattern is transferred on a gold layer to obtain nanodots. After patterning gold, a process such as a remover is lastly performed to eliminate the resist layer on the nanodots. It is possible, by undergoing the above process, to form a gold pattern characterized by being arranged and fixed at predetermined intervals on the surface of the substrate as shown in FIGS. 8A and 8B.

Figure 10A:
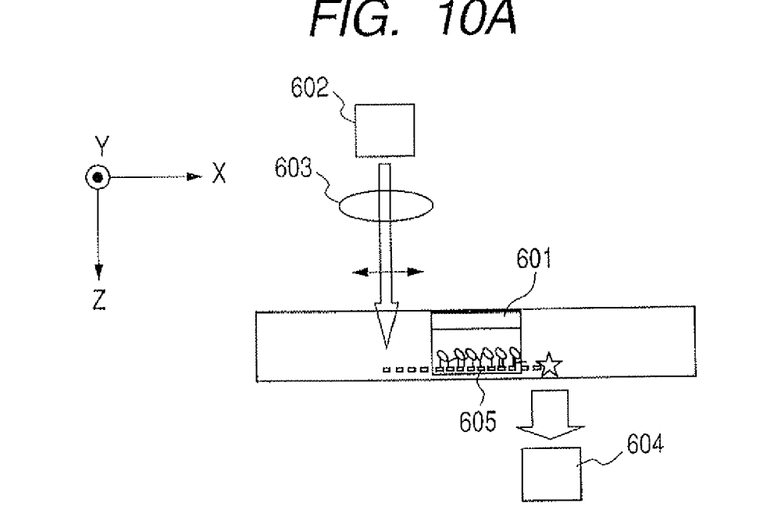
FIGS. 10A and 10B are diagrams for describing an embodiment related to the present invention.
Figure 10B:
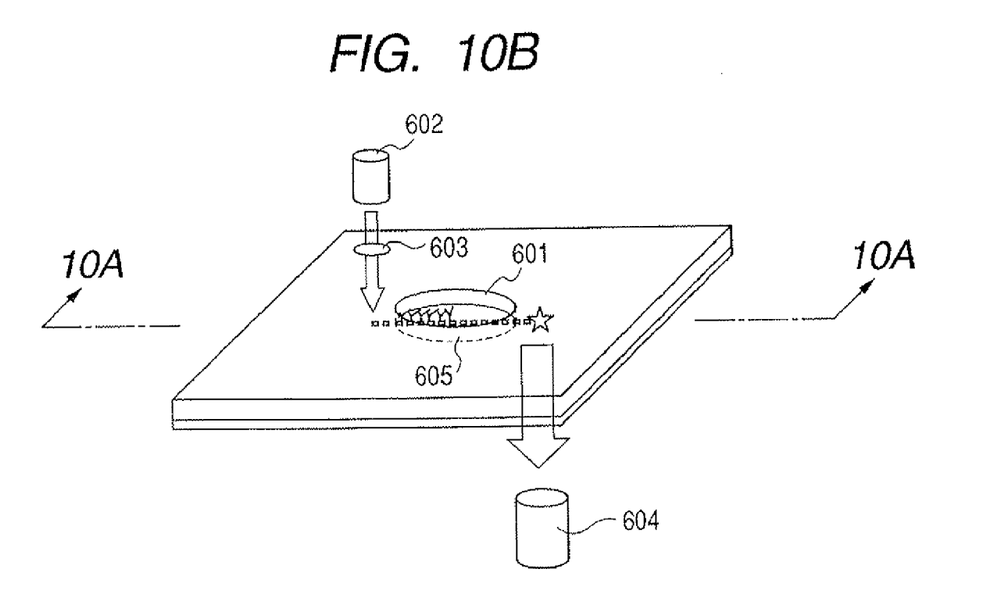

It is possible to configure a localized surface plasmon (LSPR) sensor by fixating a trapping body on the gold nanodots made in the above process. To be more specific, the trapping body which uniquely reacts to an antigen as a detecting subject is fixated on the gold nanodots so that an antibody thereof traps the antigen as a target substance. Furthermore, it is possible to form a kit for uniquely detecting the target substance by mounting a reaction well thereon (FIGS. 10A and 10B).

The antibody was fixed on the gold nanodots by using a method of modifying the antibody with an amino group and adsorbing the amino group on the gold nanodots.

Evaluation

1. Evaluation of Refractive Index Response

Figure 12:
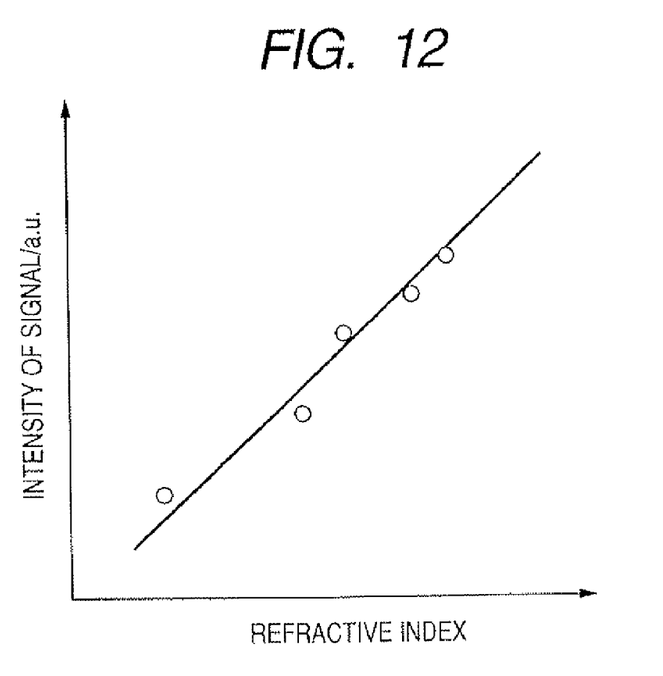
FIG. 12 is a diagram for describing an embodiment related to the present invention.

The LSPR sensor detects a change in the refractive index on the metal structure surface. Thus, the refractive index response is examined first by using solutions of different refractive indexes. FIGS. 8A and 8B show the results in the case of detecting the solutions of different refractive indexes with the LSPR sensor. It can be confirmed that the intensity of the detected light changes according to the change in the refractive index (FIG. 12).

2. Evaluation Using Antigen Antibodies

The following protocol is performed by using the kit of FIGS. 10A and 10B and setting a target substance detecting unit 605 having an anti-albumin antibody fixated thereon on the detecting device.

(1) A solution is introduced into a reaction well having a target substance detecting unit installed thereon by using a buffer solution of which pH is adjusted to 7.4. The spectrum before reaction is measured several minutes later.

(2) A sample having an albumin antigen therein is introduced into the reaction well to generate an antigen-antibody reaction.

(3) The reaction of the albumin antigen to the antibody is detected by measuring the change in spectrum intensity to evaluate how a coupling amount changes over time.

Figure 11:
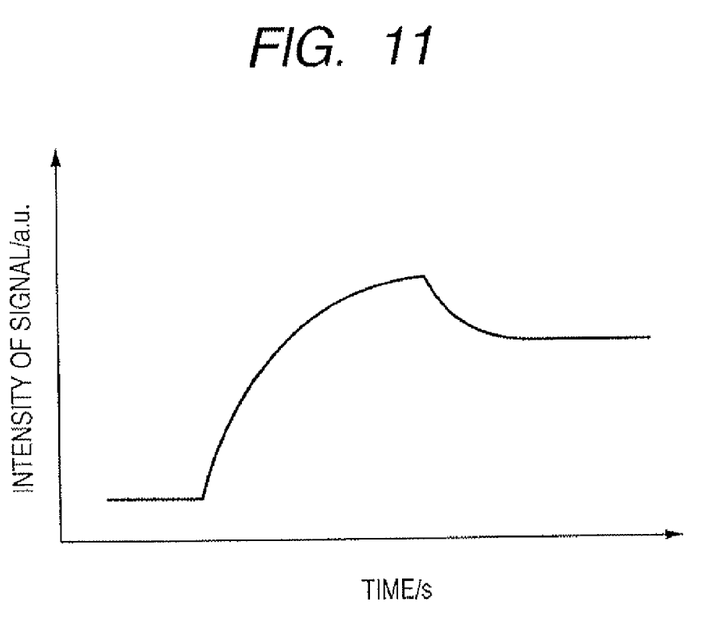
FIG. 11 is a diagram for describing an embodiment related to the present invention.

Information on kinetics as in FIG. 11 is obtained by implementing the above protocol. In the case of measuring an unknown sample, it is possible to assess information on interactions among proteins based on such databases already acquired so as to apply it in a wide variety of fields such as medical diagnostics and environmental measurement.

According to the above described preferred embodiments of the present invention, it is possible to reduce the light (background light) which enters detecting means without interacting with the metal structures belonging to the detecting unit. It is thereby possible to detect the reaction of the target substance and the trapping body with high sensitivity.

It is also possible to detect a minute amount without having a detecting signal buried in undetecting signals even on the condition that the concentration of the target substance is lean.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-077259, filed Mar. 20, 2006, and 2007-062588, filed Mar. 12, 2007, which are hereby incorporated by reference herein in their entirety.

The invention claimed is:

1. A detecting device for detecting a target substance or measuring an amount of the target substance in a sample by localized surface plasmon resonance, comprising:
   a detecting unit including a support, plural metal structures placed on the support and a trapping body for trapping the target substance in the sample;
   a light irradiation member for emitting light to irradiate the detecting unit; and
   a localized surface plasmon detector for detecting a signal based on localized surface plasmon generated by light irradiation to the detecting unit,
   wherein the plural metal structures are arranged one-dimensionally to form a transmission path on which the localized surface plasmon is one-dimensionally transmitted, and
   wherein the localized surface plasmon detector is provided at a position capable of detecting a signal based on the localized surface plasmon transmitted on the transmission path,
   wherein the localized surface plasmon detector includes a light detector for detecting the light based on the localized surface plasmon, and the light based on the plasmon transmitted on the transmission path is received by the light detector, and
   wherein the light detector has a part for converting the light based on the localized surface plasmon transmitted on the transmission path to far-field light and photoelectrically converts the converted far-field light.

2. The detecting device according to claim 1, wherein the light irradiation member is placed to have the light incident on the transmission path comprised of the one-dimensionally arranged plural metal structures so that the incident light has polarization in parallel with the transmission path.

3. The detecting device according to claim 1, wherein the light irradiation member and the light detector are placed so as not to have the same optical axis.

4. The detecting device according to claim 1, wherein the plural metal structures are arranged on a surface of the support at a pitch of array of 1 to 10 times the size of the metal structures.

5. The detecting device according to claim 1, wherein the arrangement of the metal structures is comprised of a spectrum shaping function part and a detecting function part.

6. The detecting device according to claim 1, wherein an output of the transmission path having a different number of arrangements comprised of the metal structures is detected on an equivalent condition.

7. The detecting device according to claim 1, wherein an electromagnetic field response of the metal structures has a directivity in a transmission direction.

* * * * *